United States Patent
Iwasaki et al.

(10) Patent No.: US 7,566,485 B2
(45) Date of Patent: Jul. 28, 2009

(54) MEDICAL CONTAINER

(75) Inventors: Toshiharu Iwasaki, Kawasaki (JP); Masataka Kotani, Yokohama (JP)

(73) Assignee: Hosokawa Yoko Co., Ltd., Tokyo (JP)

(*) Notice: Subject to any disclaimer, the term of this patent is extended or adjusted under 35 U.S.C. 154(b) by 448 days.

(21) Appl. No.: 10/540,128

(22) PCT Filed: Feb. 10, 2004

(86) PCT No.: PCT/JP2004/001411

§ 371 (c)(1), (2), (4) Date: Jun. 21, 2005

(87) PCT Pub. No.: WO2004/071375

PCT Pub. Date: Aug. 26, 2004

(65) Prior Publication Data

US 2006/0051534 A1   Mar. 9, 2006

Related U.S. Application Data

(60) Provisional application No. 60/455,564, filed on Mar. 19, 2003.

(30) Foreign Application Priority Data

Feb. 12, 2003   (JP)   ............................ 2003-033440

(51) Int. Cl.
*B32B 1/02*   (2006.01)
*B32B 27/08*   (2006.01)

(52) U.S. Cl. .................... 428/35.7; 428/35.2; 428/36.8; 428/516

(58) Field of Classification Search ................ 428/34.1, 428/34.8, 34.9, 35.1, 35.2, 35.4, 35.5, 35.7, 428/36.6, 36.7, 36.8, 36.92, 515, 516
See application file for complete search history.

(56) References Cited

U.S. PATENT DOCUMENTS

| 5,089,323 | A | * | 2/1992 | Nakae et al. ................ 428/220 |
| 5,478,617 | A | | 12/1995 | Watanabe et al. |
| 5,501,887 | A | | 3/1996 | Tanaka et al. |
| 5,520,972 | A | | 5/1996 | Ezaki et al. |
| 6,319,991 | B1 | | 11/2001 | Okayama et al. |
| 7,317,045 | B2 | * | 1/2008 | Zanchetta et al. ............. 524/68 |

FOREIGN PATENT DOCUMENTS

| EP | 0564206 A2 | 10/1993 |
| EP | 1241191 A1 | 9/2002 |
| JP | 5-293160 A | 11/1993 |
| JP | 6-246886 A | 9/1994 |
| JP | 6-286087 A | 10/1994 |
| JP | 7-125738 A | 5/1995 |
| JP | 8-231787 A | 9/1996 |
| JP | 9-262948 A | 10/1997 |
| JP | 10-316810 A | 12/1998 |

OTHER PUBLICATIONS

Patent Abstracts of Japan, vol. 1998, No. 02, Jan. 30, 1998 & JP 9 262948 A (Mitsui Petrochem Ind Ltd), Oct. 7, 1997, abstract.

* cited by examiner

*Primary Examiner*—Rena L Dye
*Assistant Examiner*—Walter B Aughenbaugh
(74) *Attorney, Agent, or Firm*—Sughrue Mion, PLLC

(57) ABSTRACT

A medical container produced from a film or sheet having at least one resin layer comprising a polyolefin resin composition, wherein the polyolefin resin composition comprises includes (A) at least one propylene-base polymer which is (A) a specific propylene-base polymer composition, (A) a propylene-base block copolymer and (A) a specific propylene-base block copolymer composition, and (B) an ethylene-base copolymer including an ethylene and at least one α-olefin having 4 or more carbon atoms, and the refractive index of the xylene-soluble portion of the mixture of polymers (A) and (B) is from 1.480 to 1.495.

11 Claims, No Drawings

MEDICAL CONTAINER

CROSS REFERENCE TO RELATED APPLICATIONS

The application claims the benefit of U.S. Provisional Application No. 60/455,564 filed on Mar. 19, 2003, and claims priority based on Japanese Patent Application No. 2003-033440 filed Feb. 12, 3003, the disclosures of which are all hereby incorporated by reference.

TECHNICAL FIELD

The present invention relates to a medical container, which is used by filling blood, medicament or the like in it. The application claims the benefit of U.S. provisional Application No. 60/455,564, filed Mar. 19, 2003, which is hereby incorporated by reference, and is based on Japanese Patent Application No. 2003-033440 filed on Feb. 12, 2003, which is hereby incorporated by reference.

BACKGROUND ART

A medical container for filling blood, medicament or the like is demanded not only to be, needless to say, hygienic but also to have high heat resistance capable of enduring sterilization treatment at a high temperature, transparency to enable the check of mingling of a foreign material or visual inspection of the change by blending of a medicament, impact resistance sufficiently high to prevent the bag from rupturing at falling on handling or at packaging and transportation, flexibility for facilitating the discharge of contents, and blocking resistance not to readily cause separation of film or sheet at the production of a medical container or not to contact a medicament-containing medical container with its outer packaging bag.

In particular, demands are increasing for a medical container which can be sterilized at a high temperature of 121° C. or more having a strong sterilization power, can satisfy all of heat resistance, transparency, impact resistance, flexibility and blocking resistance, and can be industrially produced.

For the medical container, a soft polyvinyl chloride, a polyethylene-base material such as high-pressure low-density polyethylene, linear low-density polyethylene, high-density polyethylene and ethylene-vinyl acetate copolymer, and a polypropylene-base material such as propylene homopolymer and random or block copolymer of propylene and other $\alpha$-olefin have been heretofore used.

The vinyl chloride-base resin is excellent in the balance of heat resistance, transparency, flexibility and impact resistance but this resin has a problem in that a plasticizer used for imparting the performance dissolves out into a medicament solution or food.

Out of polyethylene-base materials, the high-pressure low-density polyethylene is deficient in that the heat resistance or impact strength is poor. As for the linear low-density polyethylene, a polyethylene having a low density is used so as to enhance the transparency or flexibility, but when the density is decreased, insufficient heat resistance is liable to result and furthermore, problems arise, for example, the low molecular weight component of the resin lowers the blocking resistance of the container or dissolves out into a medicament. The ethylene-vinyl acetate copolymer is excellent in the transparency but disadvantageously low in the heat resistance. The high-density polyethylene is deficient in that the transparency and impact resistance are poor. Thus, polyethylene-base materials cannot satisfy a good balance of heat resistance, transparency and impact resistance.

Out of polypropylene-base materials, the propylene homopolymer and propylene random copolymer are excellent in the transparency but inferior in the blocking resistance, and the propylene block copolymer is poor in the balance of flexibility, impact resistance and transparency.

For solving these problems, with respect to the medical container using a polyethylene-base material, a multilayer container having a layer mainly comprising a high-density polyethylene and a layer mainly comprising a linear low-density polyethylene has been proposed (see, for example, JP-A-5-293160 (the term "JP-A" as used herein means an "unexamined published Japanese patent application").

Furthermore, a polyethylene-base material produced by using a metallocene-base catalyst and having excellent impact resistance and transparency has been recently developed and studies are being made to apply this material to a medical container. Also, a method of using these materials in combination and stacking two, three or more layers has been proposed (see, for example, JP-A-7-125738).

On the other hand, with respect to the medical container using a polypropylene-base material, a technique of using a resin composition comprising a propylene-base random copolymer having an $\alpha$-olefin content of 5 to 8 mass % and a mixture of specific ethylene-propylene and ethylene-butene random copolymers to obtain a container excellent in the heat resistance, transparency, impact resistance and the like has been disclosed (see, for example, JP-A-8-231787).

Also, a container having a constitution such that a layer comprising a propylene homopolymer or propylene-$\alpha$-olefin random copolymer containing from 0 to 30% of a polyethylene-base resin is provided as the outer layer and a three-layer laminate comprising a mixture of a propylene homopolymer or a propylene/$\alpha$-olefin random copolymer and an olefin-base elastomer or the like is provided as the intermediate layer has been proposed (see, for example, JP-A-9-262948).

Furthermore, a technique of using a resin composition comprising a crystalline polypropylene and a propylene/$\alpha$-olefin copolymer having a specific limiting viscosity ratio, and forming a specific morphology at the thermoformation has been proposed (see, for example, JP-A-10-316810).

However, the container described in JP-A-5-293160 cannot always hold a sufficient transparency after sterilization at a temperature of 121° C. or more and fails in fully satisfying the requirement on the market that sterilization can be performed at a higher temperature in a shorter time.

Also in the case of using the laminate described in JP-A-7-125738, the transparency after high-temperature sterilization of 121° C. or more is not sufficiently high and moreover, the impact resistance is also insufficient to readily cause rupture at the heat-welded part on falling of the container, therefore, improvements are demanded. Furthermore, a film or sheet obtained by a water cooling inflation method, a T-die method or the like has particularly a smooth surface and readily causes blocking of films or sheets with each other and when these are pulled apart, a whitened flaw remains on the surface and the outer appearance is seriously deteriorated in some cases.

The resin composition described in JP-A-8-231787 has a problem that the heat resistance and transparency are still insufficient.

The container described in JP-A-9-262948 does not have a sufficiently high impact resistance and particularly, in the case of a container having a volume of 1 L or more, the impact resistance is not satisfied from the standpoint of preventing rupture on falling.

The method described in JP-A-10-316810 has a problem in that not only the impact resistance or the thermal shrinkage percentage at the heat sterilization expresses strong anisotropy due to orientation of the domain but also stable production while keeping the quality can be hardly attained because the formation of specific morphology is sensitive to the molding conditions or the like.

The present invention has been made under these circumstances and an object of the present invention is to provide a medical container having heat resistance high enough to enable sterilization at a temperature of 121° C. or more and exhibiting excellent properties in all of the transparency, impact resistance, flexibility and blocking resistance.

DISCLOSURE OF INVENTION

As a result of extensive investigations, the present inventors have found that the above-described object can be attained by a medical container using a polyolefin resin composition containing specific components, where the xylene-soluble portion has a refractive index within a specific range. Based on this finding, the following medical container has been accomplished.

More specifically, the medical container of the present invention is produced from a film or sheet having at least one resin layer comprising a polyolefin resin composition, wherein the polyolefin resin composition comprises (A) at least one propylene-base polymer selected from the group consisting of (A1) a propylene-base polymer composition as a mixture of (A11) a propylene polymer and (A12) an ethylene-propylene copolymer elastomer, (A2) a propylene-base block copolymer, and (A3) a propylene-base block copolymer composition as a mixture of (A2) a propylene-base block copolymer and (A12) an ethylene-propylene copolymer elastomer, and (B) an ethylene-base copolymer comprising an ethylene and at least one α-olefin having 4 or more carbon atoms, and the refractive index of the xylene-soluble portion is from 1.480 to 1.495.

In the medical container of the present invention, the polyolefin resin composition preferably has a xylene-soluble portion content of 20 to 70 mass %.

Furthermore, in the polyolefin resin composition, the ratio ($MFR_A/MFR_B$) of the melt flow rate ($MFR_A$) of the propylene-base polymer (A) to the melt flow rate ($MFR_B$) of the ethylene-base copolymer (B) is preferably from 0.3 to 3.0.

The medical container of the present invention may also be produced such that the film or sheet has a first high-density polyethylene layer containing a high-density polyethylene and this first high-density polyethylene layer is disposed in the inner side.

The medical container of the present invention may also be produced such that the film or sheet has a second high-density polyethylene layer containing a high-density polyethylene and this second high-density polyethylene layer is disposed in the outer side.

In the case where the film or sheet has a first high-density polyethylene layer, the first high-density polyethylene layer preferably contains 20 mass % or more of a high-density polyethylene having a density of 0.950 $g/cm^3$ or more.

In the case where the film or sheet has a second high-density polyethylene layer, the second high-density polyethylene layer preferably contains 20 mass % or more of a high-density polyethylene having a density of 0.950 $g/cm^3$ or more.

In the medical container of the present invention, the thickness of the resin layer comprising a polyolefin resin composition preferably occupies 60% or more of the entire thickness of the film or sheet.

In the present specification, unless otherwise indicated, MFR is a value measured at 230° C. with a load of 21.18 N according to JIS K 7210.

The medical container of the present invention is presumed to have excellent properties because of the following reasons. That is, a resin component having high crystallinity is considered to impart heat resistance to the resin and a rubber-analogous resin component having low crystallinity is considered to impart the impact resistance. Usually, the refractive index greatly differs between a component having high crystallinity and a component having low crystallinity and therefore, a mixture of these components is decreased in the transparency. However, in the polyolefin resin composition for use in the medical container of the present invention, the component having low crystallinity has a specific refractive index. More specifically, the refractive index of the xylene-soluble portion presumed to contain a low crystallinity component is in a specific range and the difference in the refractive index between the low crystallinity component and the high crystallinity component is considered to become small, so that heat resistance and impact resistance can be imparted without decreasing the transparency. By using a film or sheet having at least one layer comprising this polyolefin resin composition, a medical container excellent in the transparency, impact resistance, heat resistance, flexibility and blocking resistance can be obtained.

BEST MODE FOR CARRYING OUT THE INVENTION

The present invention is described in detail below.

The medical container of the present invention is produced from a film or sheet having at least one resin layer comprising a polyolefin resin composition and has, for example, a bag form.

The polyolefin composition contains (A) a propylene-base polymer and (B) an ethylene-base copolymer and the xylene-soluble portion thereof has a refractive index of 1.480 to 1.495.

The propylene-base polymer (A) is at least one member selected from the group consisting of (A1) a propylene-base polymer composition as a mixture of (A11) a propylene polymer and (A12) an ethylene-propylene copolymer elastomer, (A2) a propylene-base block copolymer, and (A3) a propylene-base block copolymer composition as a mixture of (A2) a propylene-base block copolymer and (A12) an ethylene-propylene copolymer elastomer.

The propylene polymer (A11) (hereinafter, sometimes simply referred to as a component (A11)) contained in the propylene-base polymer composition (A1) is a propylene homopolymer or a propylene-ethylene random polymer comprising propylene and ethylene and having an ethylene content of 5 mass % or less.

The melt flow rate (hereinafter referred to as "MFR") of the propylene polymer (A11) is not particularly limited but this is preferably from 0.1 to 50 g/10 min, more preferably from 0.5 to 20 g/10 min, still more preferably from 0.5 to 5 g/10 min, because the mold processability, heat resistance and impact resistance all can be enhanced.

The ethylene-propylene copolymer elastomer (A12) (hereinafter, sometimes simply referred to as a component (A12)) contained in the propylene-base polymer composition (A1) is a copolymer elastomer substantially comprising only ethylene and propylene and having a propylene-originated unit content of 50 to 85 mass %. The MFR of the ethylene-propylene copolymer elastomer (A12) is not particularly limited but this is preferably from 0.1 to 50 g/10 min, more preferably from 0.5 to 20 g/10 min, still more preferably from 0.5 to 5 g/10 min, because the mold processability, heat resistance and impact resistance all can be enhanced.

The proportion of the propylene polymer (A11) occupying in the propylene-base polymer composition (A1) is, in view of high heat resistance, preferably from 90 to 30 mass %, more preferably from 85 to 50 mass %, still more preferably from 80 to 65 mass %, per 100 mass % in total of components (A11) and (A12).

The propylene-base block copolymer (A2) (hereinafter, sometimes simply referred to as a component (A2)) is a propylene-ethylene block copolymer obtained by melt-kneading a polymer material mixture produced through a first step of polymerizing a propylene homopolymer or a propylene and ethylene copolymer having an ethylene content of less than 5 mass % and subsequently a second step of polymerizing a propylene and ethylene copolymer having an ethylene content of 10 to 70 mass % in a polymerization vessel consisting of at least two vessels, which may be the same as or different from that used in the polymerization of the first step.

In the propylene-base block copolymer (A2), the proportion of the polymer produced in the first step is not particularly limited but this is preferably from 90 to 30 mass % and in view of profitability in the production, more preferably from 85 to 50 mass %, still more preferably from 80 to 65 mass %.

The ethylene content of the polymer obtained in the first step is usually less than 5 mass %, preferably less than 4 mass %, more preferably less than 1.5 mass %. If the ethylene content of the polymer obtained in the first step is 5 mass % or more, the heat resistance at sterilization is liable to decrease.

The ethylene content of the polymer obtained in the second step is usually from 10 to 70 mass %, preferably from 20 to 60 mass %. If the ethylene content of the polymer obtained in the second step is less than 10 mass %, the impact resistance readily decreases, whereas if it exceeds 70 mass %, the transparency sometimes decreases.

The catalyst used in the polymerization of the first and second steps is not particularly limited and, for example, a Ziegler.Natta catalyst or a metallocene catalyst is suitably used. The process for the polymerization may be any of a bulk method, a solution method, a slurry method, a vapor phase method and a combination thereof.

The propylene-base block copolymer composition (A3) (hereinafter, sometimes simply referred to as a component (A3)) is a mixture of the above-described propylene-base block copolymer (A2) and an ethylene-propylene copolymer elastomer (A12). The mixing ratio of (A2) and (A12) is, in view of high heat resistance, preferably from 90:10 to 50:50, more preferably from 80:20 to 50:50.

Among those components (A1), (A2) and (A3), the propylene-base polymer (A) is preferably the component (A2), namely, a propylene-base block copolymer, because this component expresses stable performance and is inexpensive.

The MFR of the propylene-base polymer (A) is not particularly limited but this is preferably from 0.1 to 50 g/10 min, more preferably from 0.5 to 20 g/10 min, still more preferably from 0.5 to 5 g/10 min, because the mold processability, heat resistance and impact resistance all can be enhanced.

The ethylene-base copolymer (B) (hereinafter, sometimes simply referred to as a component (B)) is a copolymer consisting of an ethylene and at least one α-olefin having 4 or more carbon atoms and mainly comprising an ethylene-originated unit (50 mass % or more). Examples of the α-olefin include 1-butene, 1-pentene, 4-methyl-1-pentene, 1-hexene and 1-octene. As the ethylene-base copolymer (B), one or more of these copolymers is(are) used.

The density (according to JIS K 7112 Method D) of the ethylene-base copolymer (B) is usually 0.915 g/cm$^3$ or less and in view of high transparency, preferably less than 0.905 g/cm$^3$, more preferably less than 0.900 g/cm$^3$.

The MFR of the ethylene-base copolymer (B) is not particularly limited but this is preferably from 0.1 to 20 g/10 min, because the mold processability, heat resistance and impact resistance all can be enhanced.

In the polyolefin resin composition containing these components (A) and (B), the refractive index of the xylene-soluble portion which dissolves in xylene at ordinary temperature is from 1.480 to 1.495, preferably from 1.480 to 1.490. When the refractive index of the xylene-soluble portion falls in this range, both the impact resistance and the transparency can be satisfactorily high. If the refractive index of the xylene-soluble portion is less than 1.480 or exceeds 1.495, the transparency decreases.

The refractive index of the xylene-soluble portion becomes higher as the density of the ethylene-base copolymer (B) increases, and becomes lower as the density of the ethylene-base copolymer (B) decreases.

The proportion and refractive index of the xylene-soluble portion are determined as follows.

A specimen (10 g) of a polyolefin resin composition is added to 1 L of an orthoxylene and after the temperature is elevated to a boiling temperature (about 135° C.) by stirring the solution under heating, the specimen is completely dissolved over 30 minutes or more. After confirming the complete dissolution with an eye, the solution is left standing with stirring to cool to 100° C. or less and held in a constant-temperature bath kept at 25° C. for 2 hours. Thereafter, the precipitated component (xylene-insoluble portion Xi) is separated by filtration through a filter paper to obtain a filtrate. The obtained filtrate is heated at a temperature of 140° C. to distill out xylene in a nitrogen stream (about 1 L/min) and the residue is dried to obtain a xylene-soluble portion Xs. At this time, the drying of xylene-insoluble portion and xylene-soluble portion is performed at 60° C. under reduced pressure for one day.

The proportion of the xylene-soluble portion is determined by (mass of Xs/mass of specimen).

The xylene-soluble portion is composed of a low molecular material in the polyolefin resin composition, a non-crystalline molecule, and the like.

In the measurement of refractive index of the xylene-soluble portion, the xylene-soluble portion is preheated at 230° C. for 5 minutes in a press-molding machine, then degassed for 30 seconds, pressed at 6 MPa for 1 minute and cooled at 30° C. for 3 minutes to obtain a film having a thickness of 50 to 80 μm. Subsequently, a specimen comprising this film is left standing at ordinary temperature for 24 hours and then measured on the refractive index for sodium D line at 23° C. by an Abbe refractive index meter (manufactured by Atago Co. Ltd.) using ethyl salicylate as the intermediate solution.

The content of the xylene-soluble portion in the polyolefin resin composition is preferably from 10 to 70 mass %, more preferably from 20 to 70 mass %. If the xylene-soluble portion content is less than 10 mass %, the impact strength at low temperatures is liable to be insufficient, whereas if it exceeds 70 mass %, the heat resistance is sometimes not satisfied.

In the polyolefin resin composition, the ratio ($MFR_A/MFR_B$) of the MFR ($MFR_A$) of the propylene-base polymer (A) to the MFR (MFR$_B$) of the ethylene-base copolymer (B) is preferably from 0.3 to 3.0, more preferably from 0.3 to 2.5, still more preferably from 0.3 to 2.0. If the MFR ratio is less than 0.3, the impact resistance at low temperatures is liable to be insufficient, whereas if it exceeds 3.0, fish eye is readily generated on the film to impair the outer appearance.

The proportion of the component (A) in the polyolefin resin composition is not particularly limited as long as the refractive index of the xylene-soluble portion is in the range from 1.480 to 1.495, but in view of higher heat resistance, this is usually on the order of 40 to 90 mass %, preferably from 50 to 70 mass %.

In the polyolefin resin composition, another polymer may be blended within the range of not impairing the object of the present invention. Specific examples of the another polymer which can be blended in the polyolefin resin composition include polyethylene-base resins such as high-pressure low-density polyethylene, linear low-density polyethylene and high-density polyethylene, various styrene-base elastomer such as styrene-butadiene elastomer and hydrogenated product thereof, random copolymers of propylene and an α-olefin having 4 or more carbon atoms, an ethylene-vinyl acetate copolymer, copolymers of ethylene and a (meth)acrylic acid (ester), and olefin-base thermo-plastic elastomers. The proportion of this another polymer contained is preferably less than 40 mass % per 100 mass % of the polyolefin resin composition.

Examples of the method for producing the polyolefin resin composition include a melt-kneading method. In the case of melt-kneading the components (A1), (A2) and (B), for example, the component (A2) may be melt-mixed after melt-mixing the components (A11), (A12) and (B). At this time, the order of melt-mixing the components (A11), (A12) and (B) is not particularly limited and the component (B) may be melt-kneaded after obtaining the component (A1) by melt-kneading the components (A11) and (A12), or the components (A11), (A12) and (B) may be simultaneously melt-kneaded. For the melt-kneading, a single-screw or twin-screw extruder can be usually used.

The thus-produced polyolefin resin composition contains (A) a propylene-base polymer and (B) an ethylene-base copolymer and the xylene-soluble portion in the polyolefin-base resin composition, which is presumed to be a low crystalline component, has a refractive index of 1.480 to 1.495, so that the resin composition can be excellent not only in the heat resistance but also in all of the transparency, impact resistance, flexibility and blocking resistance.

The film or sheet constituting the medical container has at least one resin layer comprising the above-described polyolefin resin composition. Such a film or sheet is formed by, for example, an air-cooling or water-cooling inflation molding method or a T-die method.

This film or sheet may be a single-layer film or sheet composed of a resin layer comprising the polyolefin resin composition or may be a multilayer film or sheet including a resin layer comprising the polyolefin resin composition.

The thickness of the film or sheet is usually from 30 to 1,000 μm and in view of flexibility and strength, preferably from 50 to 700 μm, more preferably from 100 to 500 μm.

In the case where the film or sheet is composed of two or more layers, by taking account of transparency, impact resistance and heat resistance, the thickness of the resin layer comprising the polyolefin resin composition preferably occupies 60% or more of the entire thickness of the film or sheet.

In the case of a multilayer film or sheet, the multilayer film can be produced by an extrusion lamination method of laminating a single layer or multilayer melt resin including at least one resin layer comprising the above-described polyolefin resin composition on a film formed of the same or different material, or by a dry lamination method of laminating a film formed of the same or different material and a single layer or multilayer body including at least one resin layer comprising the above-described polyolefin resin composition, through an adhesive.

The medical container is produced from a film or a sheet and has, for example, a bag form. This medical container may be a single chamber container or a container with multiple chambers divided by an easily separable partition part or a resin-made partition member. If desired, the medical container may be fixed with a mouth member for injection or ejection or with another medicament container for the purpose of mixed infusion, by heat-sealing or the like.

Examples of the method for producing the medical container include a method of cutting the above-described film or sheet and heat-sealing the marginal parts thereof to form a desired container shape. In this method, the order of cutting and heat-sealing may be reversed.

The heat-sealing method at the formation of the film or sheet into a container shape is not particularly limited and, for example, welding methods such as hot-plate sealing method, high-frequency sealing method and ultrasonic wave sealing method can be employed. However, the heat-sealing conditions such as heat-sealing temperature and shape of the heat-sealed part are preferably set not to impair the performance of the medical container, such as outer appearance and impact resistance.

The medical container can be easily produced when it is formed of a single layer film or sheet, and is more enhanced in the hygiene, heat resistance and the like when it is formed of a multilayer film or sheet.

Particularly, when the film or sheet is a multilayer body having a first high-density polyethylene layer containing a high-density polyethylene and the medical container is produced by disposing the first high-density polyethylene layer in the inner side, a medicament comes into contact with this first high-density polyethylene layer and therefore, not only the hygiene is more improved but also the impact resistance at low temperatures, the appearance of heat-sealed part, the strength and the like are enhanced.

Also, when the film or sheet is a multilayer body having a second high-density polyethylene layer containing a high-density polyethylene and the medical container is produced by disposing this second high-density polyethylene layer in the outer side, the impact resistance at low temperatures is enhanced. In particular, a medical container produced by disposing the second high-density polyethylene layer as the outermost layer is preferred, because blocking with the outer packaging material of the medical container hardly occurs.

Accordingly, in a more preferred embodiment, the medical container has a high-density polyethylene layer in the inner and outer sides.

Furthermore, when the film or sheet is a multilayer body having a layer containing a propylene-ethylene random copolymer and the medical container is produced by disposing this propylene-ethylene random copolymer-containing layer in the inner side and/or in the outer side, the heat resistance is more enhanced.

The high-density polyethylene contained in the first high-density polyethylene layer and the second high-density polyethylene layer is an ethylene homopolymer or an ethylene • α-olefin copolymer of ethylene and a slight amount of α-olefin having from 3 to 12 carbon atoms. Examples of the α-olefin in the ethylene• α-olefin copolymer include propylene, 1-butene, 1-pentene, 1-hexene, 4-methyl-1-pentene, 1-octene, 1-decene and 1-dodecene. These are used individually or in combination of two or more. Among these, 1-butene, 1-pentene, 1-hexene, 4-methyl-1-pentene and 1-octene are preferred.

Such a high-density polyethylene is produced by various processes such as slurry method, vapor phase method and solution method, preferably using a Ziegler•Natta catalyst or a metallocene catalyst.

The density (according to JIS K 7112. Method D) of this high-density polyethylene is usually 0.940 g/cm$^3$ or more, preferably 0.950 g/cm$^3$ or more, more preferably 0.955 g/cm$^3$ or more. If the density is less than 0.940 g/cm$^3$, insufficient heat resistance results in some cases and deformation, shrinkage or reduction of transparency may occur at the sterilization at a temperature exceeding 121° C.

The MFR (at 190° C. with a load of 21.18 N according to JIS K 7210) of the high-density polyethylene is approximately from 0.1 to 50 g/10 min, preferably from 0.5 to 20 g/10 min. With an MFR of approximately from 0.1 to 50 g/10 min, an appropriate melt tension can be obtained at the molding and a film or sheet can be easily formed.

In the first and second high-density polyethylene layers, another polymer may be blended within the range of not impairing the objet of the present invention. Specific examples of the another polymer include polyethylene resins such as high-pressure low-density polyethylene and linear low-density polyethylene, polypropylene resins such as propylene homopolymer, propylene•α-olefin random copolymer and propylene•α-olefin block copolymer, various styrene-base elastomers such as styrene-butadiene elastomer, ethylene•propylene elastomer, an ethylene-vinyl acetate copolymer, copolymers of ethylene and (meth)acrylic acid (ester), and olefin-base thermoplastic elastomers. The another polymer is blended for the purpose of, for example, adjusting the peel strength at the marginal part of a medical container or at the easily separable partition part of a multiple chamber container.

In the case of blending another polymer, the high-density polyethylene having a density of 0.950 g/cm$^3$ or more is preferably contained in an amount of usually 20 mass % or more, preferably 30 mass % or more, more preferably 70 mass % or more, still more preferably 90 mass % or more in each of the first and second high-density polyethylene layers. As long as the high-density polyethylene having a density of 0.950 g/cm$^3$ or more is contained in an amount of 20 mass % or more, heat sterilization at 121° C. or more can be performed even when the first or second high-density polyethylene layer is provided, and moreover, the blocking resistance of film is more enhanced.

The preferred thickness of each of the first and second high-density polyethylene layers varies depending on the high-density polyethylene content but when the high-density polyethylene is contained in an amount of 90 mass % or more, the thickness is preferably from 5 to 40 μm.

The finally obtained medical container is used by filling a medicament and then subjecting it to steam sterilization under high pressure. The steam sterilization temperature is not particularly limited but this is generally from 100 to 140° C. Other known sterilization methods such as ultraviolet ray and electron beam can also be used in combination with the high-temperature high-pressure heat sterilization.

The thus-obtained medical container is produced from a film or sheet comprising the above-described polyolefin-base resin composition and therefore, exhibits excellent property not only in the heat resistance but also in all of the transparency, impact resistance, flexibility and blocking resistance. In particular, even when sterilized at 121° C. or more having a high sterilization effect, excellent property is exhibited in all of the transparency, impact resistance, flexibility and blocking resistance and therefore, this medical container is useful.

In any of the resin materials for use in the medical container, commonly employed known additives can be appropriately blended within the range of not impairing the effect of the present invention, if desired, such as antistatic agent, antioxidant, lubricant, anti-blocking agent, anti-clouding agent, nuclear agent, organic and inorganic pigments, ultraviolet absorbent, dispersing agent and reinforcing agent (e.g., talc, calcium carbonate) However, the blending amount thereof must be within the range admitted in the medical field and in particular, these additives are preferably not blended in a layer which comes into direct contact with the contents.

EXAMPLES

The present invention is described in greater detail below by referring to Examples, however, the present invention is not limited to these Examples. In the following description, unless otherwise indicated, the percentage "%" is on a mass basis.

Examples 1 to 9 and Comparative Examples 1 to 5

<Resin Material>
The resins used in Examples and Comparative Examples are as follows.

[Propylene Polymer (A11)]

A11-1:
Propylene homopolymer (PL300A produced by SunAllomer Ltd.); MFR: 1.7 g/10 min, xylene-soluble content: 0.5%.

A11-2:
Propylene-ethylene random copolymer having, an ethylene content of 3 mass % (PB222A produced by SunAllomer Ltd.); MFR: 0.8 g/10 min, xylene-soluble content: 3.1%.

[Ethylene-Propylene Copolymer Elastomer (A12)]

A12-1:
Ethylene-propylene copolymer (Tafmer P0680 produced by Mitsui Chemicals, Inc.); MFR: 0.7 g/10 min, density: 0.885 g/cm$^3$.

[Propylene-Base Block Copolymer (A2)]

A2-1:
Propylene-ethylene block copolymer obtained through a first-step polymerization and a second-step polymerization, which is a propylene-ethylene block copolymer containing 75% of a propylene homopolymer obtained in the first step and 25% of a propylene-ethylene copolymer having an ethylene content of 35% obtained in the second step; MFR: 1.0 g/10 min, xylene-soluble content: 26%. This copolymer A2-1 was produced as follows.

(1) Preparation of Solid Catalyst
In a nitrogen atmosphere, 56.8 g anhydrous magnesium chloride was completely dissolved at 120° C. in 100 g of absolute ethanol, 500 mL of petrolatum oil "CP15N" produced by Idemitsu Kosan Co., Ltd. and 500 mL of silicone oil "KF96" produced by Shin-Etsu Silicone Co., Ltd. The resulting solution was stirred at 120° C. and 5,000 revolutions/min for 2 minutes by using TK Homomixer manufactured by Tokushu Kika Kogyo Co., Ltd. While continuing the stirring, the solution was transferred to 2 liter of anhydrous heptane by taking care not to exceed 0° C., thereby precipitating a white solid. The white solid obtained was thoroughly washed with anhydrous heptane, vacuum-dried at room temperature and then partially deprived of ethanol in nitrogen stream. Subsequently, 30 g of $MgCl_2 \cdot 1.2C_2H_5OH$ obtained as a spherical solid was suspended in 200 mL of anhydrous heptane and thereto, 500 mL of titanium tetrachloride was added dropwise over 1 hour with stirring at 0° C. Thereafter, the suspension was heated and when reached 40° C., 4.96 g of diisobutyl phthalate was added. Then, the temperature was elevated to 100° C. over about 1 hour. After the reaction at 100° C. for 2 hours, the solid portion was sampled by hot filtration, 500 mL of titanium tetrachloride was added to this reaction product, and the resulting mixture was stirred and then reacted at 120° C. for 1 hour. After the completion of reaction, the solid portion was again removed by hot filtration and washed 7 times with 1.0 liter of hexane at 60° C. and then 3 times with 1. 0 liter of hexane at room temperature to obtain a solid catalyst. The titanium content in the solid catalyst component obtained was measured and found to be 2.36 mass %.

(2) Prepolymerization

Into a 3-liter autoclave, 500 mL of n-heptane, 6.0 g of triethylaluminum, 0.99 g of cyclohexylmethyldimethoxy-silane and 10 g of polymerization catalyst obtained above were charged in a nitrogen atmosphere and stirred at a temperature of 0 to 5° C. for 5 minutes. Subsequently, propylene was supplied to the autoclave such that 10 g of propylene was polymerized per 1 g of the polymerization catalyst, and prepolymerization was performed at a temperature of 0 to 5° C. for 1 hour. The prepolymerization catalyst obtained was washed 3 times with 500 mL of n-heptane and then used in the following main polymerization.

(3) Main Polymerization (First Step: Production of Propylene Homopolymer)

Into an autoclave equipped with a stirrer and having an inner volume of 60 liter, 2.0 g of a prepolymerization solid catalyst prepared as above, 11. 4 g of triethylaluminum and 1.88 g of cyclohexylmethyldimethoxysilane were charged in a nitrogen atmosphere. Thereto, 18 kg of propylene and hydrogen in an amount of 5,000 mol ppm based on the propylene were charged and after elevating the temperature to 70° C., the polymerization was performed for 1 hour. After 1 hour, unreacted propylene was removed to complete the polymerization.

(Second Step: Production of Propylene-Ethylene Copolymer)

After the completion of first-step polymerization, liquid propylene was removed and subsequently, hydrogen and an ethylene/propylene (26/74 (by mass)) mixed gas of 2.2 $Nm^3$/hour were supplied at 75° C. to have a hydrogen concentration of 40,000 mol ppm based on the total amount of ethylene, propylene and hydrogen, and then the polymerization was performed for 60 minutes. Thereafter, unteacted gas was removed to complete the polymerization. As a result, 6.6 kg of a polymer material mixture was obtained.

To 100 parts by mass of the polymer material mixture obtained above, 0.30 parts by mass of phenol-base antioxidant and 0.1 part by mass of calcium stearate were added and mixed by a Henschel mixer at room temperature for 3 minutes. The resulting mixture was melt-kneaded by an extruder having a screw aperture of 40 mm (Nakatani Model VSK 40-mm Extruder) at a cylinder temperature set to 210° C. to obtain propylene-ethylene block copolymer (A2-1) pellets.

A2-2:

Propylene-ethylene block copolymer obtained through a first-step polymerization and a second-step polymerization, which is a propylene-ethylene block copolymer containing 80% of a propylene-ethylene random copolymer having an ethylene content of 2% obtained in the first step and 20% of a propylene-ethylene copolymer having an ethylene content of 50% obtained in the second step; MFR: 1.0 g/10 min, xylene-soluble content: 26%. This copolymer A2-2 was produced as follows.

(First Step: Production of Propylene-Ethylene Random Copolymer)

Into an autoclave equipped with a stirrer and having an inner volume of 60 liter, 2.0 g of a prepolymerization solid catalyst prepared in the same manner as in Production of A2-1, 11.4 g of triethylaluminum and 1.88 g of cyclohexyl-methyldimethoxysilane were charged in a nitrogen atmosphere. Thereto, 18 kg of propylene, 120 L of ethylene and hydrogen in an amount of 6,500 mol ppm based on the propylene were charged and after elevating the temperature to 70° C., the polymerization was performed for 1 hour. After 1 hour, unreacted propylene was removed.

(Second Step: Production of Propylene-Ethylene Copolymer)

The polymerization was performed in the same manner as in Production of A2-1 except that an ethylene/propylene mixed gas at a mass ratio of 44/56 and hydrogen in an amount of giving a concentration of 40,000 mol ppm were supplied and after performing the polymerization for 40 minutes, unreacted gas was removed to complete the polymerization. By this production method, 5.7 kg of a polymer material mixture was obtained.

From this polymer material mixture, propylene-ethylene block copolymer (A2-2) pellets were obtained in the same manner as in Production of A2-1.

[Ethylene-Base Copolymer (B)]

B-1:

Ethylene-1-butene copolymer (EBM2021P produced by JSR); MFR: 2.6 g/10 min, density: 0.88 $g/cm^3$.

B-2:

Ethylene-1-butene copolymer (Tafmer A4085 produced by Mitsui Chemicals, Inc.); MFR: 6.7 g/10 min, density: 0.88 $g/cm^3$.

B-3:

Ethylene-1-butene copolymer (EBM3021P produced by JSR); MFR: 2.6 g/10 min, density: 0.86 $g/cm^3$.

B-4:

Ethylene-1-butene copolymer (Engage 8480 produced by DuPont Dow Elastomers Japan K.K.), MFR: 2 g/10 min, density: 0.902 $g/cm^3$.

[Other Component]

PE1:

High-density polyethylene, density: 0.955 $g/cm^3$, MFR: 3.0 g/10 min.

PE2:

Linear low-density polyethylene, density: 0.905 $g/cm^3$, MFR: 1.0 g/10 min.

<Measurement of Physical Properties of Resin Material>

MFR:

MFR of each component of propylene-base polymer (A) and MFR of ethylene-base copolymer (B) were measured at 230° C. with a load of 21.18 N according to JIS K 7210. MFR of high-density polyethylene and linear low-density polyethylene was measured at 190° C. with a load of 21.18 N according to JIS K 7210.

Density:

This was measured according to JIS K 7112 Method D.

Xylene-soluble content:

This was measured by the method described in Mode for Carrying Out the Invention.

Refractive Index:

This was measured by the method described in Mode for Carrying Out the Invention.

<Production of Polyolefin Resin Composition>

The resin materials described above were blended at the compositional ratio shown in Table 1, mixed by Henschel mixer for 3 minutes and then melt-kneaded at temperature of 230° C. by using a single screw extruder to obtain pellets of polyolefin resin composition. The physical properties of this polyolefin resin composition are shown in Table 2.

<Production of Film>

The polyolefin resin composition pellets obtained above were molded into a tubular film having an entire thickness of 250 μm by a water cooling inflation three-layer molding machine at a temperature of 230° C. Incidentally, in the case where the tubular film was a two-layer film, the inner layer was formed to a thickness of 20 μm, and in the case of a three-layer film, the inner layer and the outer layer both were formed to a thickness of 20 μm.

Separately, a single layer film was molded to have a thickness of 250 μm by a water cooling inflation molding machine.

<Production of Medical Container and Sample for Measurement>

Tubular films in the state that respective inner surfaces were superposed were cut into a length of 20 cm and a width of 20 cm and then the length direction and the width direction each was heat-sealed in a seal width of 10 mm. In the inside thereof, 500 mL of water was filled to produce a bag-shaped medical container. At this time, the heat sealing was performed by using a hot-plate heat-sealing machine (a heat sealer manufactured by Tester Sangyo Co,. Ltd.) under a pressure of 0.4 MPa at a seal temperature or 170° C. for a sealing time of 1 second. The obtained medical container was subjected to a sterilization treatment at 121° C. for 30 minutes and used as a sample for measurement of the following various physical properties. However, the sample for the evaluation of blocking resistance only was subjected to a sterilization treatment at 121° C. in the state that respective inner layers were almost contacted by filling 2 mL of water into the inside and extracting the inner air by means of a vacuum pump.

TABLE 1

| | Propylene-Base Polymer (A) | | | | | | | Ethylene-Base Polymer (B) | | |
|---|---|---|---|---|---|---|---|---|---|---|
| | Propylene Polymer (A11) | | Ethylene-Propylene Copolymer Elastomer (A12) | | Propylene-Base Block Copolymer (A2) | | | | | |
| Composition No. | Resin | Proportion (mass %) | Resin | Proportion (mass %) | Resin | Proportion (mass %) | MFR (g/10 min) | Resin | MFR (g/10 min) | Proportion (mass %) |
| Composition 1 | A11-1 | 49 | A12-1 | 21 | | | 0.9 | B-1 | 2.6 | 30 |
| Composition 2 | | | | | A2-1 | 80 | 1 | B-1 | 2.6 | 20 |
| Composition 3 | | | | | A2-1 | 70 | 1 | B-1 | 2.6 | 30 |
| Composition 4 | | | | | A2-1 | 95 | 1 | B-3 | 2.6 | 5 |
| Composition 5 | | | | | A2-1 | 45 | 1 | B-4 | 2.0 | 55 |
| Composition 6 | A11-1 | 90 | A12-1 | 5 | | | 1 | B-1 | 2.6 | 5 |
| Composition 7 | | | | | A2-1 | 60 | 1 | B-2 | 6.7 | 40 |
| Composition 8 | | | | | A2-1 | 60 | 3 | B-3 | 1.8 | 40 |
| Composition 9 | A11-1 | 60 | A12-1 | 40 | | | 0.9 | | | |

TABLE 2

| | Xylene-Soluble Portion (Xs) | | |
|---|---|---|---|
| Composition No. | Refractive Index | Proportion (mass %) | MFR Ratio[1] |
| Composition 1 | 1.485 | 48 | 0.34 |
| Composition 2 | 1.482 | 42 | 0.38 |
| Composition 3 | 1.484 | 49 | 0.38 |
| Composition 4 | 1.475 | 31 | 0.38 |
| Composition 5 | 1.496 | 68 | 0.5 |
| Composition 6 | 1.485 | 11 | 0.38 |
| Composition 7 | 1.490 | 54 | 0.15 |
| Composition 8 | 1.481 | 55 | 1.67 |
| Composition 9 | 1.479 | 21 | — |

[1]MFR (at 230° C.) of propylene-base polymer (A)/MFR (at 230° C.) of ethylene-base copolymer (B)

<Measurement of Various Physical Properties>

The measurement results of the following various physical properties are shown in Table 3.

[Heat Resistance]

The appearance of the container after sterilization treatment was evaluated with an eye and judged as follows.

o: No deformation and no crinkling.

x: Deformed and many crinkles.

[Impact Resistance]

The container after sterilization treatment was cooled at 4° C. and five containers held horizontally were dropped on a hard floor from a height of 100 cm. The number of ruptured containers was counted.

[Transparency]

The container after sterilization treatment was measured on the light transmittance by using U-3300 manufactured by Hitachi Ltd. according to Transparency Test in Test Methods for Plastic Containers of The Japanese Pharmacopoeia, 14th ed.

[Blocking Resistance]

The container after sterilization treatment was left standing at 23° C. for 24 hours and then inner surfaces were pulled apart. The degree of power necessary for the separation and the separated surface state were observed with an eye and judged as follows. o: Readily separated. x: Not separated.

inner and outer sides, therefore, the heat resistance and blocking resistance were insufficient.

INDUSTRIAL APPLICABILITY

The medical container of the present invention has heat resistance high enough to enable sterilization at a temperature of 121° C. or more and at the same time, exhibits excellent properties in all of the transparency, impact resistance, flexibility and blocking resistance.

TABLE 3

|  | Film | | | | | Impact | | |
| --- | --- | --- | --- | --- | --- | --- | --- | --- |
|  | Number of Layers | Inner Layer | Intermediate Layer | Outer Layer | Heat Resistance | Resistance (number of ruptured bags) | Light Transmittance (%) | Blocking Resistance |
| Example 1 | 1 | — | Composition 1 | — | o | 0 | 79 | o |
| Example 2 | 1 | — | Composition 2 | — | o | 0 | 77 | o |
| Example 3 | 1 | — | Composition 3 | — | o | 0 | 80 | o |
| Example 4 | 3 | PE 1 | Composition 3 | PE 1 | o | 0 | 79 | o |
| Example 5 | 2 | — | Composition 8 | PE 1 | o | 0 | 74 | o |
| Example 6 | 3 | PE 1(70%) + PE2(30%) | Composition 6 | PE 1 | o | 0 | 76 | o |
| Example 7 | 3 | PE 1 | Composition 7 | PE 1 | o | 0 | 68 | o |
| Example 8 | 3 | PE 1 | Composition 3 | A11-2 | o | 0 | 82 | o |
| Example 9 | 3 | A 11-2 | Composition 8 | A11-2 | o | 0 | 78 | o |
| Comparative Example 1 | 1 | — | Composition 4 | — | o | 1 | 78 | o |
| Comparative Example 2 | 1 | — | Composition 5 | — | o | 0 | 45 | o |
| Comparative Example 3 | 1 | — | Composition 9 | — | o | 5 | 46 | o |
| Comparative Example 4 | 3 | PE 1 | Composition 5 | PE 1 | o | 0 | 51 | o |
| Comparative Example 5 | 3 | PE 2 | Composition 4 | PE 2 | x | 0 | 44 | x |

The medical containers of Examples 1 to 9 were produced from a film comprising a polyolefin resin composition containing (A) a propylene-base polymer and (B) an ethylene-base polymer and moreover, the xylene-soluble portion of the polyolefin resin composition had a refractive index of 1.480 to 1.495, therefore, these containers were excellent in the heat resistance, impact resistance, transparency and blocking resistance.

On the other hand, in the medical containers of Comparative Examples 1, 2 and 4, the xylene-soluble portion of the polyolefin resin composition had a refractive index out of the range from 1.480 to 1.495 and therefore, the transparency was low.

Furthermore, the medical container of Comparative Example 3 was produced from a film comprising a polyolefin resin composition of only propylene-base polymer (A) and moreover, the xylene-soluble portion of the polyolefin resin composition had a refractive index out of the range from 1.480 to 1.495, therefore, the transparency and impact resistance were low.

In the medical container of Comparative Example 5, the xylene-soluble portion of the polyolefin resin composition had a refractive index out of the range from 1.480 to 1.495 and therefore, the transparency was low. Moreover, a layer comprising a linear low-density polyethylene was provided in the

The invention claimed is:

1. A medical container produced from a film or sheet having at least one resin layer comprising a polyolefin resin composition, wherein said polyolefin resin composition comprises (A) at least one propylene-base polymer selected from the group consisting of (A1) a propylene-base polymer composition as a mixture of (A11) a propylene polymer and (A12) an ethylene-propylene copolymer elastomer, (A2) a propylene-base block copolymer, and (A3) a propylene-base block copolymer composition as a mixture of (A2) a propylene-base block copolymer and (A12) an ethylene-propylene copolymer elastomer, and (B) an ethylene-base copolymer comprising an ethylene and at least one α-olefin having 4 or more carbon atoms, and the refractive index of the xylene-soluble portion of the mixture of polymers (A) and (B) is from 1.480 to 1.495; and the film or sheet further comprises at least one of a first high-density polyethylene layer, which comprises a high-density polyethylene and is disposed in an inner side of the film or sheet, and a second high-density polyethylene layer, which comprises a high-density polyethylene and is disposed in an outer side of the film or sheet.

2. The medical container as claimed in claim 1, wherein said polyolefin resin composition has a xylene-soluble portion content of 20 to 70 mass%.

3. The medical container as claimed in claim 1, wherein in said polyolefin resin composition, the ratio ($MFR_A/MFR_B$) of the melt flow rate ($MFR_A$) of propylene-base polymer (A) to the melt flow rate ($MFR_B$) of ethylene-base copolymer (B) is from 0.3 to 3.0.

4. The medical container as claimed in claim 1, wherein said first high-density polyethylene layer contains 20 mass% or more of a high-density polyethylene having a density of 0.950 g/cm$^3$ or more.

5. The medical container as claimed in claim 1, wherein said second high-density polyethylene layer contains 20 mass% or more of a high-density polyethylene having a density of 0.950 g/cm$^3$ or more.

6. The medical container as claimed in claim 1, wherein the thickness of the resin layer comprising a polyolefin resin composition occupies 60% or more of the entire thickness of the film or sheet.

7. The medical container as claimed in claim 4, wherein the density of the high-density polyethylene is a value which is measured according to JIS K 7112 Method D.

8. The medical container as claimed in claim 5, wherein the density of the high-density polyethylene is a value which is measured according to JIS K 7112 Method D.

9. The medical container as claimed in claim 3, wherein the MFR is obtained as a value which is measured at 230° C. with a load of 21.18 N according to JIS K 7210.

10. The medical container as claimed in claim 2, wherein the xylene-soluble portion content is determined by a method including:

adding 10 g of a polyolefin resin composition to 1 L of an orthoxylene;

stirring the mixture at a temperature of a boiling point of the orthoxylene to dissolve the resin composition completely to obtain a solution;

cooling the solution while stirring until the temperature of the solution is 100° C. or less and keeping the solution in a constant-temperature bath at 25° C. for 2 hours;

separating a xylene-insoluble portion deposited in the solution by filtration to obtain a filtrate;

removing xylene from the filtrate by conducting drying at 60° C. under reduced pressure for one day subsequent to heating at a temperature of 140° C. in a nitrogen stream, to obtain a xylene-soluble-portion;

measuring the mass of the xylene-soluble portion; and obtaining the xylene-soluble portion content by the formula: (a mass of the xylene-soluble portion)/(mass of the added polyolefin resin composition).

11. The medical container as claimed in claim 1, wherein a refractive index of the xylene-soluble portion is determined by a method comprising:

forming a film having a thickness of 50 to 80 μm with a press-molding machine by preheating the xylene-soluble portion at 230° C. for 5 minutes, degassing for 30 seconds, pressing the xylene-soluble portion at 6 MPa for 1 minute and cooling at 30° C. for 3 minutes;

standing the film at ordinary temperature for 24 hours; and measuring a refractive index of the xylene-soluble portion as a refractive index for sodium D line at 23° C. by an Abbe refractive index meter using ethyl salicylate as the intermediate solution.

* * * * *